(12) United States Patent
Hogan

(10) Patent No.: US 7,248,907 B2
(45) Date of Patent: Jul. 24, 2007

(54) CORRELATION OF CONCURRENT NON-INVASIVELY ACQUIRED SIGNALS

(76) Inventor: Josh N. Hogan, 620 Kingwood Way, Los Altos, CA (US) 94022

( * ) Notice: Subject to any disclaimer, the term of this patent is extended or adjusted under 35 U.S.C. 154(b) by 0 days.

(21) Appl. No.: 11/254,965

(22) Filed: Oct. 19, 2005

(65) Prior Publication Data

US 2006/0089548 A1   Apr. 27, 2006

Related U.S. Application Data

(60) Provisional application No. 60/621,417, filed on Oct. 23, 2004, provisional application No. 60/621,366, filed on Oct. 23, 2004.

(51) Int. Cl.
*A61B 5/00* (2006.01)
*G01B 9/02* (2006.01)
(52) U.S. Cl. ............... 600/316; 600/310; 600/476; 356/450

(58) Field of Classification Search ............... 600/310, 600/316, 322, 473, 476; 356/450, 451, 456, 356/477, 479
See application file for complete search history.

(56) References Cited

U.S. PATENT DOCUMENTS 6,725,073 B1 *   4/2004   Motamedi et al. .......... 600/316
6,728,571 B1 *   4/2004   Barbato ...................... 600/478

* cited by examiner

*Primary Examiner*—Eric F. Winakur

(57) ABSTRACT

A non-invasive imaging and analysis system suitable for measuring attributes of a target, such as the blood glucose concentration of tissue, includes an optical processing system which provides a probe and reference beam. It also includes a means that applies the probe beam to the target to be analyzed, combines the probe and reference beams interferometrically, detects concurrent interferometric signals and correlates the detected signals with previously stored electronic data to determine the attribute of the target.

44 Claims, 9 Drawing Sheets

CORRELATION OF CONCURRENT NON-INVASIVELY ACQUIRED SIGNALS

CROSS REFERENCES TO RELATED APPLICATIONS

This application Ser. No. 11/254,965, claims priority from U.S. provisional application Ser. No. 60/621,366 titled "Parallel three dimensional analysis system" filed on Oct. 23, 2004. This application also claims priority from U.S. provisional application Ser. No. 60/621,417 titled "High speed parallel depth analysis system" filed on Oct. 23, 2004.

This application relates to U.S. patent application Ser. No. 11/025,698 filed on Dec. 29, 2004 entitled "A Multiple Reference Non-invasive Analysis System", the contents of which are incorporated by reference as if fully set forth herein. This application also relates to utility patent application Ser. No. 10/870,121 filed on Jun. 17, 2004 entitled "A Non-invasive Analysis System", the contents of which are incorporated by reference as if fully set forth herein. This application also relates to utility patent Ser. No. 10/870,120 filed on Jun. 17, 2004 entitled "A Real Time Imaging and Analysis System", the contents of which are incorporated by reference as if fully set forth herein.

FIELD OF THE INVENTION

The invention relates to non-invasive analysis in general and in particular to optical non-invasive analysis of bio-medical targets such as, tissue, organs and tooth material. This invention also relates to non-destructive defect analysis and verification of the authenticity of documents.

BACKGROUND OF THE INVENTION

Non-invasive analysis, which for purposes of this application includes non-destructive analysis, is a valuable technique for acquiring information about systems or targets without undesirable side effects, such as damaging the system being analyzed. Non-invasive analysis has a broad range of applications including, non-destructive analysis of artifacts for defects, verification of the authenticity of documents, such as, bank notes, bio-metric analysis and bio-medical analysis of living entities. In the case of analyzing living entities, such as human tissue, undesirable side effects of invasive analysis include the risk of infection along with pain and discomfort associated with the invasive process.

In the particular case of measurement of blood glucose levels in diabetic patients, it is highly desirable to measure the blood glucose level frequently and accurately to provide appropriate treatment of the diabetic condition as absence of appropriate treatment can lead to potentially fatal health issues, including kidney failure, heart disease or stroke. A non-invasive method would avoid the pain and risk of infection and provide an opportunity for frequent or continuous measurement.

Non-invasive analysis systems based on several techniques have been proposed. These techniques include: near infrared spectroscopy using both transmission and reflectance; spatially resolved diffuse reflectance; frequency domain reflectance; fluorescence spectroscopy; Polarimetry and Raman spectroscopy.

These techniques are vulnerable to inaccuracies due to issues such as, environmental changes, presence of varying amounts of interfering contamination, skin heterogeneity and variation of location of analysis. These techniques also require considerable processing to de-convolute the required measurement, typically using multi-variety analysis and have typically produced insufficient accuracy and reliability.

A correlation between blood glucose concentration in diabetics and non-invasively measured tissue optical scattering coefficient has been clearly demonstrated, for example in papers published in Optics Letters, Vol. 19, No. 24, Dec. 15, 1994 pages 2062-2064 and OPTICS LETTERS/Vol. 22, No. 3/Feb. 1, 1997 pages 190-192.

This correlation has been proposed as the basis for non-invasive glucose monitoring by involving optical coherence tomography (OCT). This proposed technique depends on a relationship between the slope of the OCT signal and the tissue scattering coefficient or measuring a change in an optical path length with glucose concentration. This approach is described in Proceedings of SPIE, Vol. 4263, pages 83-90 (2001), OPTICS LETTERS/Vol. 26, No. 13/Jul. 1, 2001, Phys. Med. Biol. 48 (2003) 1371-1390 and U.S. Pat. No. 6,725,073 issued Apr. 20, 2004 and U.S. Pat. No. 5,710,630 issued Jan. 20, 1998.

The OCT approach described uses a Super-luminescence diode (SLD) output beam that has a broad bandwidth and short coherence length. OCT analysis involves splitting the SLD output beam into a probe and reference beam (or a first portion of the primary light and a second portion of the primary light). Only a reference beam derived from the same SLD that produced the probe beam can produce interferometrically meaningful signals when combined with the probe related light. The probe beam is applied to the system to be analyzed (the target). Light scattered back from the target is combined with the reference beam to form the measurement signal.

Because of the short coherence length only light that is scattered from a depth within the target such that the total optical path lengths of the probe and reference are equal combine interferometrically. Thus the interferometric signal provides a measurement of the scattering value at a particular depth within the target.

By varying the length of the reference path length, a measurement of the scattering values at various depths can be measured and thus the scattering value as a function of depth can be measured. The profile of the scattering signal as a function of depth is referred to as the OCT signal and the slope or rate of change of the scattering signal as a function of depth is referred to as the slope of the OCT signal.

Accurate correlation between the slope of the OCT signal and the scattering coefficient relies on simplifying assumptions, such as that on average, uniform scattering throughout the tissue. In actual tissue, the scattering elements are cellular membranes and have a highly non-uniform distribution. In a practical device, distortion of the tissue and relative motion between the tissue and the monitoring device also disrupt the correlation between the slope of the OCT signal and the scattering coefficient.

In OCT systems depth scanning is achieved by modifying the relative optical path length of the reference path and the probe path. The relative path length is modified by such techniques as electro-mechanical based technologies, such as galvanometers or moving coils actuators, rapid scanning optical delay lines and rotating polygons. All of these techniques involve moving parts, which have limited scan speeds and present significant alignment and associated signal to noise ratio related problems.

Motion occurring within the duration of a scan can cause significant problems in correct signal detection. If motion occurs within a scan duration, motion related artifacts will be indistinguishable from real signal information in the detected signal, leading to motion related noise or inaccuracies in the measurement of the slope of the OCT signal. Long physical scans, for larger signal differentiation or locating reference areas, increase the severity of motion artifacts and their disruptive effect on correlation between the slope of the OCT signal and glucose concentration.

Non-moving part solutions, include acousto-optic scanning, can be high speed, however such solutions are costly, bulky and have significant thermal control and associated thermal signal to noise ratio related problems. Optical fiber based OCT systems also use piezo electric fiber stretchers. These, however, have polarization rotation related signal to noise ratio problems and also are physically bulky, are expensive and require relatively high voltage control systems.

OCT approaches to measuring glucose concentration typically focus the SLD output beam into the target tissue to perform a depth scan and then repeatedly translate a beam steering mechanism to get multiple depth scans at different locations. The OCT signal is averaged over these multiple scans and the slope of the averaged OCT signal is used to determine the glucose concentration.

The sequential nature of the multiple scan approach further exacerbates the noise related to motion artifacts that is problematic in conventional low speed scanning mechanisms. Using multiple SLDs in parallel to address this problem introduces an un-acceptable cost burden and does not address the fundamental distorting effect of motion on the slope of the OCT signal.

Transient or time varying physical changes in the tissue being analyzed due to, for example, physical compression arising from stress or stress gradients or temperature changes or temperature gradients can cause transient distortions in the depth structure, which can be different for different depth scan locations. Such transient changes can affect the slope of the OCT signal and can do so in a manner that is different for scans at different scan locations.

Furthermore, the non-uniform distribution of scatterers in tissue distorts the slope of the OCT signal within depth scans and between depth scans at different locations (even without motion or transient disruptions). This non-uniform distribution of scatterers in tissue has a disruptive effect on correlation between the slope of the OCT signal and glucose concentration, which is based on only an approximate model. These disruptive interfering influences reduce or randomize the correlation between the slope of the OCT signal and glucose concentration and make using the slope of the OCT signal, or measuring optical path lengths, as the basis for the glucose concentration measurement vulnerable to signal blurring noise.

These aspects cause the conventional approach of using the slope of the OCT signal, or measuring optical path lengths, for monitoring glucose concentration to have significant undesirable signal to noise characteristics and present problems in practical implementations with sufficient accuracy, compactness and robustness for commercially viable and clinically accurate devices. These problematic aspects also present difficulties is using OCT non-invasive analysis for a broad range of applications.

Therefore there is an unmet need for a commercially viable, compact, robust, non-invasive device with sufficient accuracy, precision and repeatability for performing non-invasive analysis such as, measuring analyte concentrations, and in particular measuring glucose concentration in human tissue.

SUMMARY OF THE INVENTION

The invention is a method, apparatus and system for non-invasive analysis. It is suitable for determining attributes of targets, such as concentrations of specific components or analytes within a target, including the concentration of glucose within human tissue. The invention includes an optical source and an optical processing system which provides probe and reference radiation. It also includes a means that applies the probe beam to the target to be analyzed, re-combines the probe and reference beams interferometrically, to generate concurrent interferometric signals which are detected and correlated with previously stored electronic data to determine an attribute of the target.

DETAILED DESCRIPTION OF THE INVENTION

Figure 1:
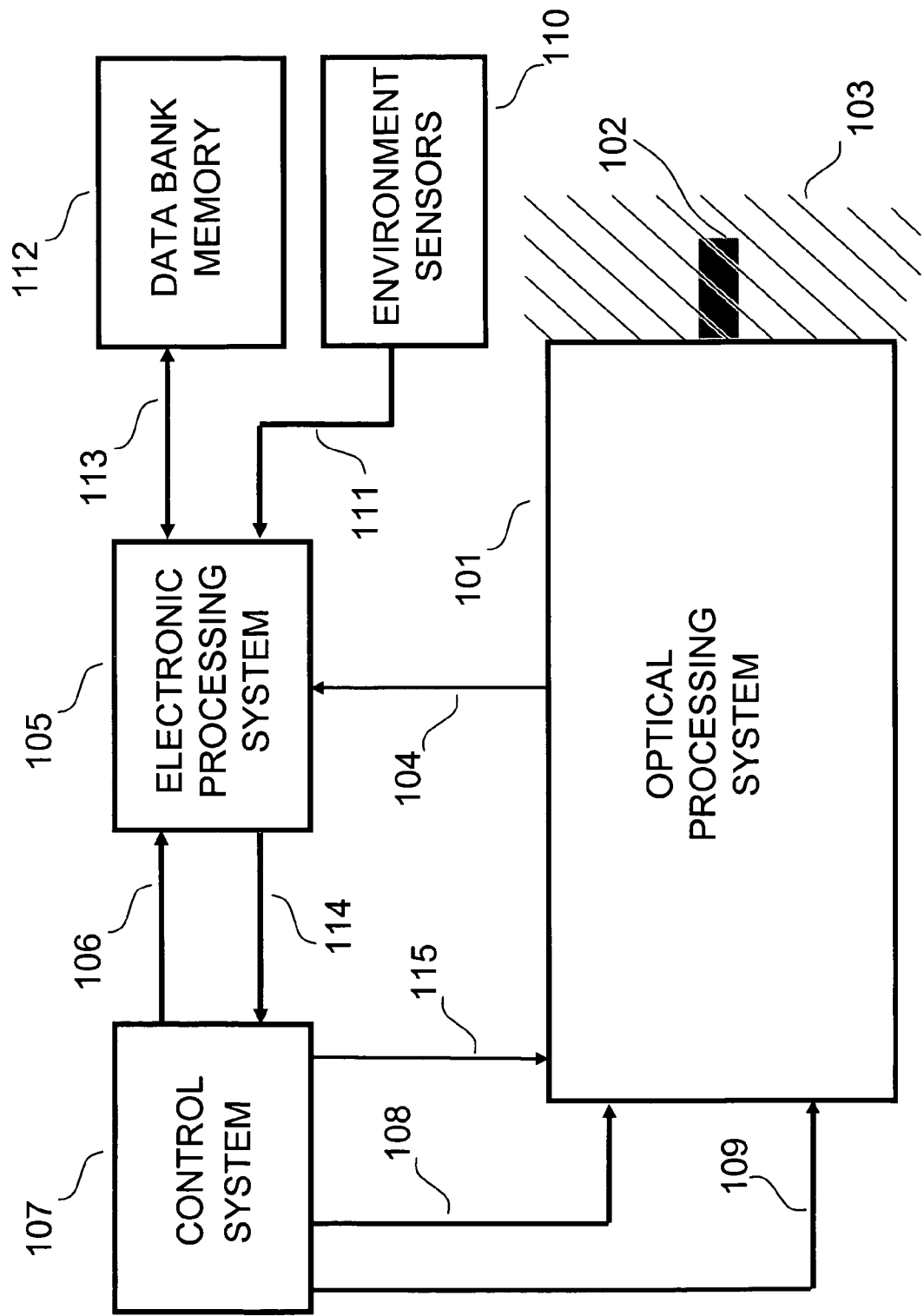
FIG. 1 is an illustration of the non-invasive analysis system according to the invention.

Optical coherence tomography is a non-invasive analysis technique based on splitting the output of a broadband optical source into a probe beam and a reference beam and of varying the optical path length of the reference beam to depth scan the target, such as tissue, and thereby generating an OCT signal of the depth scan. In the particular application of using OCT to analyze blood glucose, a change in an optical path length is measured sequentially at multiple depths, or the slope of the OCT signal of multiple depth scans is averaged, to determine the concentration of an glucose, in tissue (the target).

These approaches have problems and limitations related to issues that include motion artifacts, transient physical changes non-uniform scatterer distribution and in any event are based on approximate models. For purposes of this invention motion artifacts, includes any interfering or blurring effects of relative motion between an optical analysis system and a target and also relative motion between various components of the target.

An alternative non-invasive optical analysis approach, which addresses these problems and limitations includes applying radiation to the tissue to be analyzed; detecting multiple interference signals from multiple depths within the target concurrently, thereby avoiding motion artifacts; normalizing the detected spatially separated interference signals to compensate for transient physical characteristics and signal level variations; correlating the normalized detected spatially separated interference signals with data previously stored in a data bank to generate correlation data; and processing the correlation data to determine the glucose concentration level.

Advantages of this novel approach include acquiring complete sets of interference signals concurrently, thus avoiding motion related issues, and correlating the interference signal data set with previously stored data sets, rather than measuring an optical data path change or the slope of an OCT signal and assuming a simplified model of the target. The interference signals represent characteristics or attributes of the tissue (the target) that are modified by the glucose concentration. Correlating data sets (or maps of data) with reference data sets (or fiducial maps of data) does not require making simplistic assumptions or using an approximate model.

Correlating data sets with reference fiducial maps of data does not assume a uniform distribution of scatters, which allows more accurate representation of actual tissue. In general, correlating a data set with fiducial maps does not require an accurate understanding or description of the mechanism that causes the interference signals. Ideally, other factors that influence the interference signals can be compensated for by means of environment sensors and the attribute of the target that is to be determined has a dominant effect on the interference signals.

For purposes of this application concurrently includes simultaneously or at a high speed with respect to motion artifacts. Similarly concurrent signals includes simultaneous signals and also signals occurring at a high speed with respect to motion artifacts, thereby making such signals insensitive to motion artifacts. For purposes of this application an environment sensor is any sensor that measures a factor that also affects the interference signals.

Techniques for acquiring interference signals from multiple depths, either simultaneously or at high speed and therefore concurrently are described in patent applications incorporated herein by reference. These techniques include: simultaneously generating interference signals corresponding to different depths in a manner that different signals have different frequency content and therefore can be separated by electronic filtering; and high speed electronic scanning using two mode-locked lasers that are mode-locked frequency at different frequencies.

Advances in power levels of optical sources, such as superluminescent diodes (SLDs) or laser diodes, enable using broad area collimated probe radiation (rather than low power focused radiation) and still getting sufficient backscattered radiation to use a multi-segment detector in order to detect multiple spatially separated interference signals simultaneously. Optionally, one or more masks or micro lens arrays may be used to further isolate and reduce overlap of interference signals to individual segments. This provides the opportunity to acquire multiple spatially separated interference signals in parallel.

Sets of concurrent signals from various depths and from multiple spatially separated locations of the target can be acquired either by using broad area radiation to generate multiple probe beams or by sequentially translating a single narrow probe beam to the different spatially separated locations. In general such a probe beam or probe beams are referred to as probe radiation. The various depths from which signals are to be analyzed would be determined by characteristics of the reference radiation or by timing signals.

Ideally the various depths determined would accurately and repeatedly correspond to corresponding depths in the tissue being monitored. In practical use, the tissue may be distorted by, for example, the pressure of applying the monitor to skin. Such distortions can be compensated for by measuring the distorting influence. For example, including strain gauges to measure stresses and using these measurements to compensate for the distorting influences. Compensation can be achieved by adjusting the nominal depth to account for such distortions.

Also, ideally using fixed intensity probe radiation would accurately and repeatedly result in the same probe intensity at the various depths and spatial locations. In practical use, changes in skin surface, deviations from normal incidence of the probe radiation with respect to the skin surface and distorting influences, such as pressure, all contribute to modifying the actual probe intensity reaching different depths and spatial locations. These modifying influences can be compensated for by measuring the influences and compensating for them by adjusting the measured intensities of the various interference signals detected.

Techniques for achieving compensation include but are not limited to the following: measuring the intensity at one depth (for example the skin surface) and using the difference between the resulting value and the expected value to derive or access a set of modifying factors for the different depths; measuring the average intensity at a set of depths and using the difference between the resulting value and the expected value to derive or access a set of modifying factors for the different depths; comparing the intensities at different spatial locations with the same nominal depth and deriving adjustment factors.

In general these compensating techniques are herein referred to as normalizing the detected spatially separated interference signals. The resulting set of normalized signal intensities constitute a normalized interference signal map of the tissue. This interference signal map can then be correlated with a data bank stored in memory. The data bank contains reference data sets or fiducial maps of glucose level data corresponding to different normalized interference signals at the various depths and spatial locations.

Storing a significant personalized data bank in low cost consumer devices has been made practical by advances in storage mechanisms such as flash memory. Alternately the data bank may be stored in remote memory, such as disc based memory, and communication with the electronic processing system accomplished by, for example, wireless cellular phone technology or over the Internet.

The fiducial maps stored in the data bank are generated in a previous calibration process whereby the actual glucose level is measured accurately by an already calibrated glucose concentration measuring system while (over a period of time that the glucose level is known) the device is applied to one or more specific tissue locations and the interference signal intensities at the various depths and spatial locations and the effects are measured. Alternatively, the fiducial maps could be generate by an on-going measurement process that produces calibration data by processing measurement data over significant periods of time.

During the calibration process, the values of different disturbing influences are also measured and correction factors related to the disturbing influences (or environmental sensor data) are generated. The glucose levels and correction factors are stored, for example, at memory addresses related to the intensities of the interference signals. Figure of merit data is also stored.

Already calibrated systems include, but are not limited to, systems that involves a direct blood analysis method, such as a conventional finger pricking system or more elaborate professional level invasive or non-invasive systems. These calibration measurements are repeated at a number of different glucose levels. Various adaptive or learning algorithms can be used to ensured the stored data will provide accurate glucose measurements when correlated with new interference signal measurements.

Intensities at additional glucose levels that were not measured can be generated by interpolating or extrapolating from the measured levels. Calibration can be performed in a comprehensive manner over a relatively short period of time while the glucose level is regularly monitored and varies over a large range. Alternatively, calibration could be performed over an extended period of time with intermittent use of an already calibrated glucose measuring system. During the extended calibration period, the un-calibrated device could be used to monitor trends only.

The level of accuracy of the device being calibrated can be monitored and viewed by means of the figure of merit. The figure of merit can indicate when the device being calibrated has sufficient accuracy to be used independently as a reliable glucose measuring or monitoring device, i.e. when it is sufficiently calibrated. Similarly, the figure of merit can indicate when re-calibration is required.

Correlating the normalized detected spatially separated interference signals with the fiducial maps from the data bank can include, but is not limited to, addressing the data bank with an address that is a combination of a specific depth at a specific spatial location and the intensity of the corresponding normalized detected spatially separated interference signal. The data output from the selected address is fiducial map data that can include, but is not limited to, glucose level and weighting factor data.

The resulting fiducial map data is processed to determine the glucose concentration, or in general, the characteristics of the target are correlated with the fiducial maps stored in the data bank to determine an attribute of the target. Determining the analyte concentration by processing the fiducial map data can include, but is not limited to the following: calculating a weighted average of all of the glucose levels ensuing from the fiducial map data; establishing an acceptable glucose level band, excluding fiducial map data that lies outside the acceptable glucose level band and recalculating a weighted average of a reduced set of glucose levels ensuing from the fiducial map data; repeating the whole process multiple times and averaging the results.

The resulting fiducial map data may also be processed to provide a figure of merit for the degree of correlation between the various measurements. This figure of merit can be stored and monitored over time to provide a measure of the degree to which the original calibration remains valid and also may be used to indicate when re-calibration is desirable. In the case that calibration has been performed at multiple tissue sites, this figure of merit may also be used to indicate the preferred site or to indicate that a specific tissue site should not be relied on.

Tissue sites may be identified by locating characteristics or marks including, but not limited to, finger prints, freckles or edges of skin blemishes, artificial marks such as tattoos. For purposes of this application these characteristics are referred to as registration marks. Various techniques can be used to ensure correct alignment with the locating marks. For example, a magnified image of the target area, derived from the multi segment detector or from a conventional charged coupled device (CCD) detector, can be displayed on a display (such as a liquid crystal display or one based on thin film technology (LCD or TFT)) along with an ideally located image to assist in manual positioning the monitor.

The difference information between the images could also be used to automatically position the monitor. Information from strain gauges and/or the multi segment detector could be used to adjust the tilt orientation of the monitor to achieve substantially normal radiation of the skin surface. Other position and orientation indicators such as a set of blinking light emitting diodes (LEDs) could be used. For example, the LEDs could be arranged around edge of the monitor, the blinking frequency could indicate the direction in which to move and the LED intensities could be an indication of orientation with respect to normal.

The radiation for generating the positioning image can be the same as used for analyzing the glucose concentration of the tissue or can be radiation from a different source, such as an LED. Interference between the two radiation sources can be prevented by pulsing both sources with a phase offset between the pulses. Pulsing the analyzing radiation may also be used to suppress interference from background radiation. Pulsing the analyzing radiation may also be used to generate higher peak power and thereby provide improved signal to noise ratios which provides more accurate scattering coefficient measurements which lead to a more accurate glucose concentration measurement.

A preferred embodiment of the invention is illustrated in and described with respect to FIG. 1 where a non-invasive analysis system is shown. The following description relates to the specific glucose monitoring application of the invention, however, the invention has a broad range of applications. In general the invention is a method, apparatus and system for determining an attribute of a target. In the glucose application the target is tissue and the attribute to be determined is the glucose level.

In the preferred embodiment, an optical processing system 101 generates probe radiation 102 and applies a portion of it to a target 103 which generates back-scattered radiation, which is interferometrically analyzed by the optical processing system and resultant interference signals are detected by an opto-electronic detector. In the preferred embodiment the probe radiation is broad area radiation and the detector is a multi-segment detector. The resultant electronic signals 104 are fed to an electronic processing system 105.

The electronic processing system 105 also receives timing signals 106 from a control system 107 which controls the optical source and multiple modulating reflective elements in the optical processing system 101 by means of electronic control signals 108 and modulating signals 109. The electronic processing system 105 also receives data, by means of electronic environment sensor signals 111, from environmental sensors 110, which can include measuring, surface pressure, blood pressure and temperature.

The electronic processing system 105 also retrieves previously stored data from data bank memory 112, such as flash or disc memory, which contains correction data to compensate for varying sensor readings and also contains fiducial maps of glucose level data that correspond to various combinations of detected interference signals and sensor readings. The electronic processing system 105 communicates with the data bank memory 112 by means of an address/data bus 113 that is a conventional address/data bus or in the case of a remote data bank by, for example, wireless cellular phone technology, herein also referred to as an address/data bus.

The electronic processing system 105 also processes the detected signals and sensor readings to align the optical processing system 101 with registration marks on the target. This may be accomplished by providing electronic alignment data 114 to the control system 107 which then uses this data to generate alignment control signals 115 which align the optical processing system 101 with respect to the registration marks.

The electronic processing system 105 processes the detected interference signals 104, the environment sensor signals 111 and the data from the data bank memory 112 to calculate the glucose level of the aligned target. This processing may be done iteratively with alignment adjustments. Alternatively alignment can be done electronically by measuring the mis-alignment and re-mapping the spatial intensity distribution of the multi-segment detector.

This alternate alignment approach can be optimized by using multi-segment detectors with a large number of detector segments. Processing can occur in either the analog or digital domain or can occur in a combination of both. For example, detected interference signals could be normalized to modify for intensity variations in the analog domain and then the normalized signal digitized and further processed to modify for environmental sensor signals (or information or data) in the digital domain.

Many combinations of analog and digital processing are possible. For purposes of this application, when referring to aspects such as, interference signal or environmental signal, the words "signal", "information" and "data" are interchangeable. Also normalization of signals or information can occur before or after spatial separation, or can be partially before and partially after spatial separation.

The electronic processing system 105 repeatedly processes the aligned detected interference signals 104, the environment sensor signals 111 and the data from the data bank memory 112 to calculate the glucose level of the target at frequent intervals. The response time of glucose levels to changing circumstances in humans is typically of the order of minutes or tens of minutes. Calculating, also referred to as, measuring or monitoring, the glucose level at intervals of the order of minutes or tens of minutes effectively constitutes continuous monitoring of the glucose level.

Figure 2:
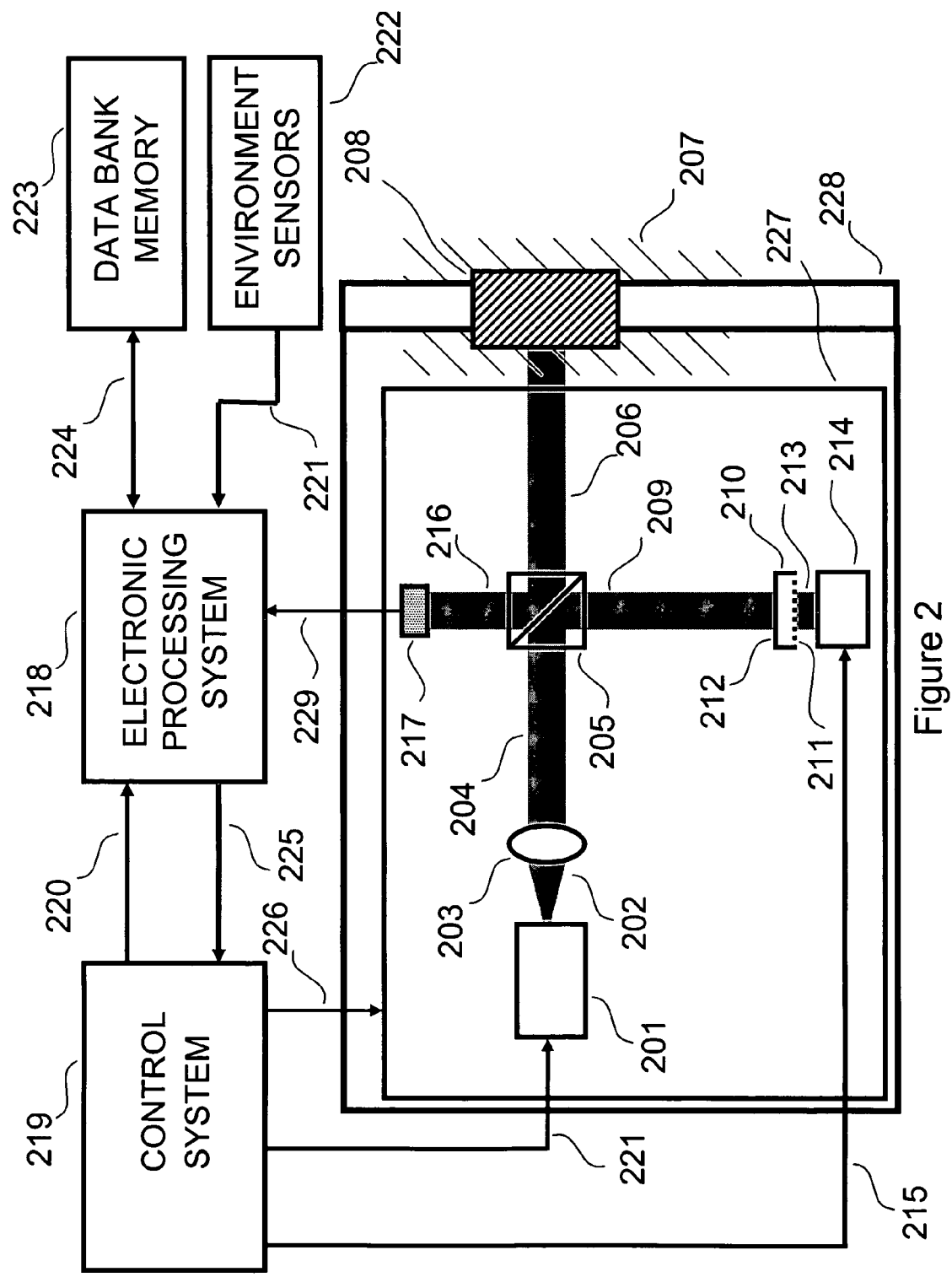
FIG. 2 is a more detailed illustration of the non-invasive analysis system.

The preferred embodiment is illustrated in more detail in FIG. 2. An optical source 201, such as, an SLD, an LED or a mode-locked laser, generates radiation 202 which is collimated to be broad area radiation by an optical lens 203 (or an optical lens system). The collimated broad area radiation 204 is directed through a beam-splitter 205 and a first portion of the collimated broad area radiation 206, which is probe radiation, is applied to the target 207 by means of an optional steering mirror 208 to generate back-scattered radiation within the target.

A second portion 209 of the broad area radiation 204, is directed by the first beam-splitter 205 to a partially reflective mirror 210 which has a partial reflective surface 211 and a anti-reflective coated surface 212 where the transmitted portion is applied to a modulating reflective element 214. The combination of the partially reflective surface 211 and the modulating reflective element 214 generates composite reference radiation which, when combined with the back-scattered radiation will generate multiple interference signals corresponding to different depths within the target.

The modulating frequency of the modulating reflective element 214 is controlled by the control signal 212. As described in the patent applications incorporated herein by reference, the multiple interference signals have different frequency content which enables the signals corresponding to different depths to be separated by electronic filtering to provide information from the different depths concurrently, and therefore with reduced or no sensitivity to motion. The relative optical path lengths between the multiple depths is determined by the distance between the partially reflective surface 211 and the modulating reflective element 214.

The modulated reference radiation is directed back to the first beam-splitter 205 (which also acts as a beam-combiner), where it is combined with a portion of the back-scattered radiation generated in the target, to produce a set of concurrent interferometric signals 216 which are detected by the opto-electronic detector 217. The opto-electronic detector is a multi-segment detector illustrated further in FIG. 3 which detects spatially separated interference signals.

The output signals from the multi-segment detectors, i.e. the spatially separated interference signals 229, are fed to the processing system 218. The control system 219 controls the optical source 201 and the modulating reflective element 214 by means of the signals 221 and 215. The control system 219 also supplies the processing system 218 with timing signals 220 that allow the processing system to separate information associated with interference signals corresponding to different depth locations.

This electronic filtering allows spatially separated information, corresponding to different depths, to be extracted from each of the interference signals (or composite interference signal) detected by the multi-segment detector.

The processing system 218 also receives environmental signals 231 from sensors 222 such as strain gauges and temperature sensors located on the surface of the target. The environmental signals provide depth correction data with which to adjust the nominal depth signals to compensate for the influence of the environmental factors.

This may be accomplished by using the depth correction data in conjunction with the nominal depth location data and spatial location as address data for retrieving previously stored depth correction data from the memory data bank 223 by means of a conventional address/data bus 224. The retrieved depth correction data is used to either modify sample timing signals or correct the measured interference signal intensities or a combination of both.

The processing system 218 also intensity corrects the detected spatially separated interference signals. Intensity correction may be accomplished by comparing the measured interference signal intensities at depths that are not affected by glucose (or analyte) concentration, such as at or near the surface of the tissue, and generating intensity correction data that is used in conjunction with the depth location data and spatial location as address data for retrieving previously stored intensity correction data from the memory data bank 223.

The processing system 218 then normalizes the detected spatially separated interference signals by combining the intensity correction data and the depth correction data with the measured intensities of the detected spatially separated interference signals. The normalized detected spatially separated interference signal intensities are correlated with data from a data bank stored in memory and containing fiducial maps of glucose level data previously stored.

This can be accomplished by using the normalized detected spatially separated interference signal intensities data, with the depth location data and spatial location, as address data for retrieving previously stored correlation data, or fiducial maps, from the memory data bank 223. Correlation data includes glucose level data and weighting factor data.

The correlation data is processed to determine the glucose level or concentration (the attribute) of the tissue (the target) by calculating a weighted average of all of the glucose levels ensuing from the correlation data, establishing an acceptable glucose level band, excluding glucose levels that lie outside the acceptable glucose level band and re-calculating a weighted average of a reduced set of glucose levels.

The correlation data can also be processed to align the probe signal with respect to locating characteristics or marks on the skin surface. This can be accomplished by analyzing the spatial correlation of interference signals, from the multi-segment detectors, associated with the skin surface and generating alignment information 225 which is sent to the control system 219.

The control system generates alignment signals 226 which are used to move the optical processing system 227 with respect to a frame 228 by conventional means, such as electro-mechanical means. Various methods of translating the optical probe radiation with respect to the target registration marks are illustrated and described in the patent applications referenced by and incorporated into this application.

The complete detection and processing of the interference signals can be repeated multiple times to calculate an average glucose level. If necessary, re-alignment can be performed between or during processing. Repeated complete cycles of processing constitute continuous glucose level monitoring.

Figure 3B:
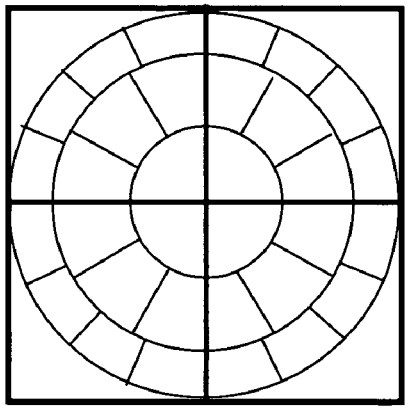
FIG. 3 illustrates multi-segment detectors, a mask and a micro lens array.
Figure 3D:
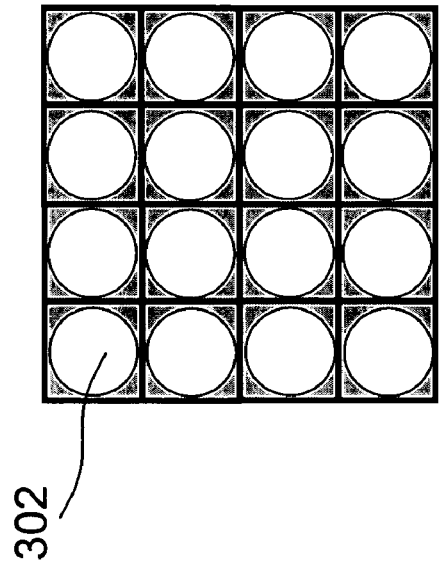
Figure 3A:
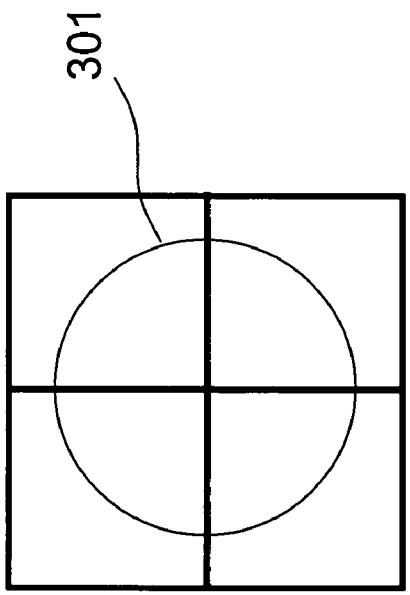

FIG. 3A illustrates a multi-segment detector four quadrant opto-electronic detector (similar in design to the commonly used in optical data storage drives), which would typically be centered on the back-scattered radiation from a circular probe beam of radiation. Each of the segments, one of which is indicated by 301, is equally sensitive to a quadrant of interference signals resulting from the backscattered signals in that they are of equal area and have a symmetrical spatial relationship with the backscattered radiation.

Figure 3C:
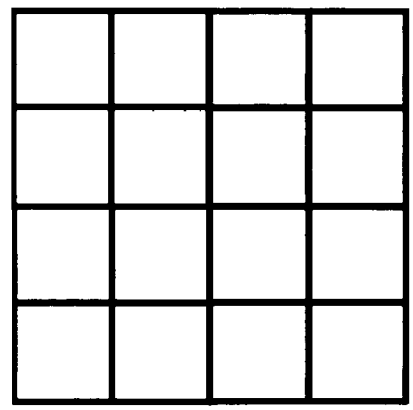

FIG. 3B illustrates an example of a detector with a greater number of segments which do not all have equal areas. The detailed design can be optimized, for example, to match the area of segments to the energy profile of the probe radiation, or to match the outer segments to characteristics of the registration marks. FIG. 3C illustrates a conventional N×M detector array (in the example, a 4×4 array). Such arrays can be fabricated with a significantly larger number of elements matching increasing optical source powers. With large arrays, the outputs of multiple detector segments may be grouped together to increase effective detector segment area.

This grouping can be performed dynamically as a method of aligning the optical processing system in response to processing information relating to the registration marks. This alignment approach does not require physical re-positioning of the optical processing, but may also used in conjunction with physical re-positioning. For example, dynamic grouping could be used during re-alignment by repositioning which eventually achieves alignment compatible with a standard grouping.

FIG. 3D illustrates a mask, which consists of an array of holes, one of which is indicated by 302, surrounded by opaque material, that is suitable for use with the detector array of FIG. 3C. One or more masks can be used to reduce interference or overlap of signals between different detector segments. FIG. 3D also illustrates a micro-lens array, one of which micro-lens is indicated by 302.

Such a micro-lens array is suitable for focusing radiation onto the multi-segment detectors. A similar micro-lens array with a long Raleigh range is suitable for focusing radiation into the target. Other mask and micro-lens array designs can include holes or lenses with different areas to help equate optical power by having larger diameter holes or lenses toward the outer portions of the optical radiation beam.

Figure 4B:
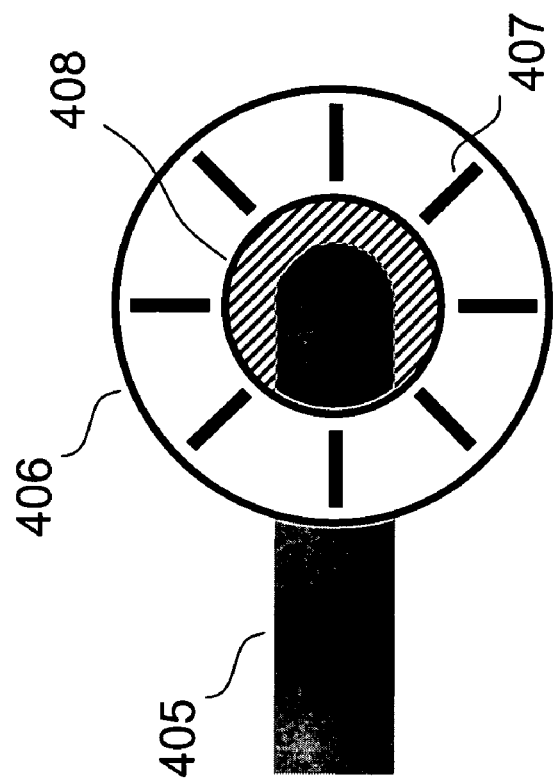
FIG. 4 illustrates a steering mirror mounted in a housing with environment sensors.
Figure 4A:
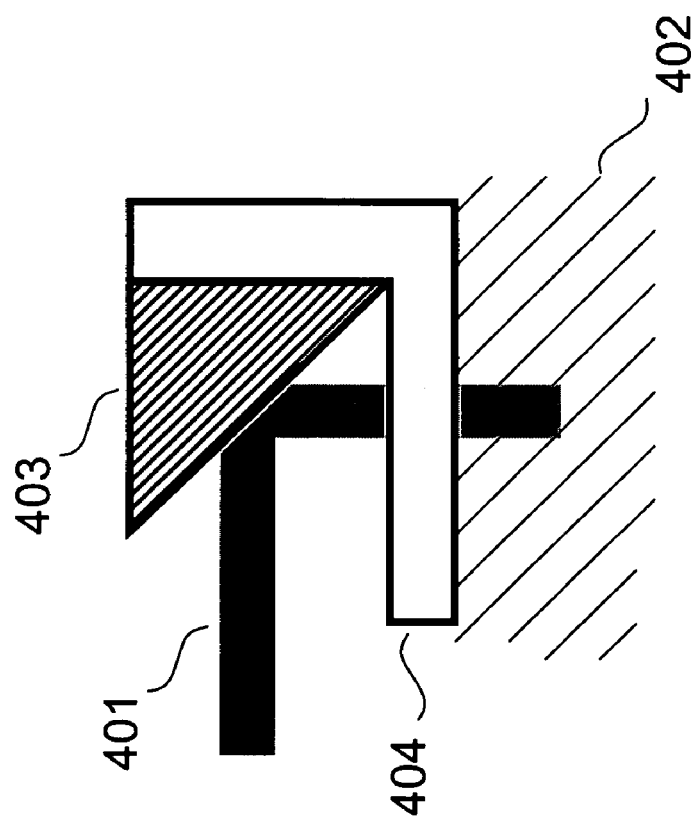

FIG. 4 illustrates an arrangement for applying the probe radiation 401 to the target 402 by means of the beam steering mirror 403 (which was 208 of FIG. 2). The probe radiation 401 is directed to the target 402 through an aperture (which may be a transparent window) in the rigid housing 404. The view from the under-side side of the housing 404, which can be in direct physical contact with the target is illustrated in FIG. 4B.

In FIG. 4B the probe radiation 405 is shown centered in the aperture in the center of the housing. The illustrated under-side of the of the housing 406 (which may be deformable) has embedded strain gauges, one of which is indicated by 407, such as bonded metallic strain gauges or semiconductor pressure-sensitive diffused strain gages. The housing 406 may also contain other environment sensors, such as a temperature sensor 408 which can be a thermocouple junction in thermal contact with ring located around the aperture and which is in thermal contact with the target. The electrical outputs of the environmental sensors are made available to the electronic processing system 105 of FIG. 1.

Figure 5:
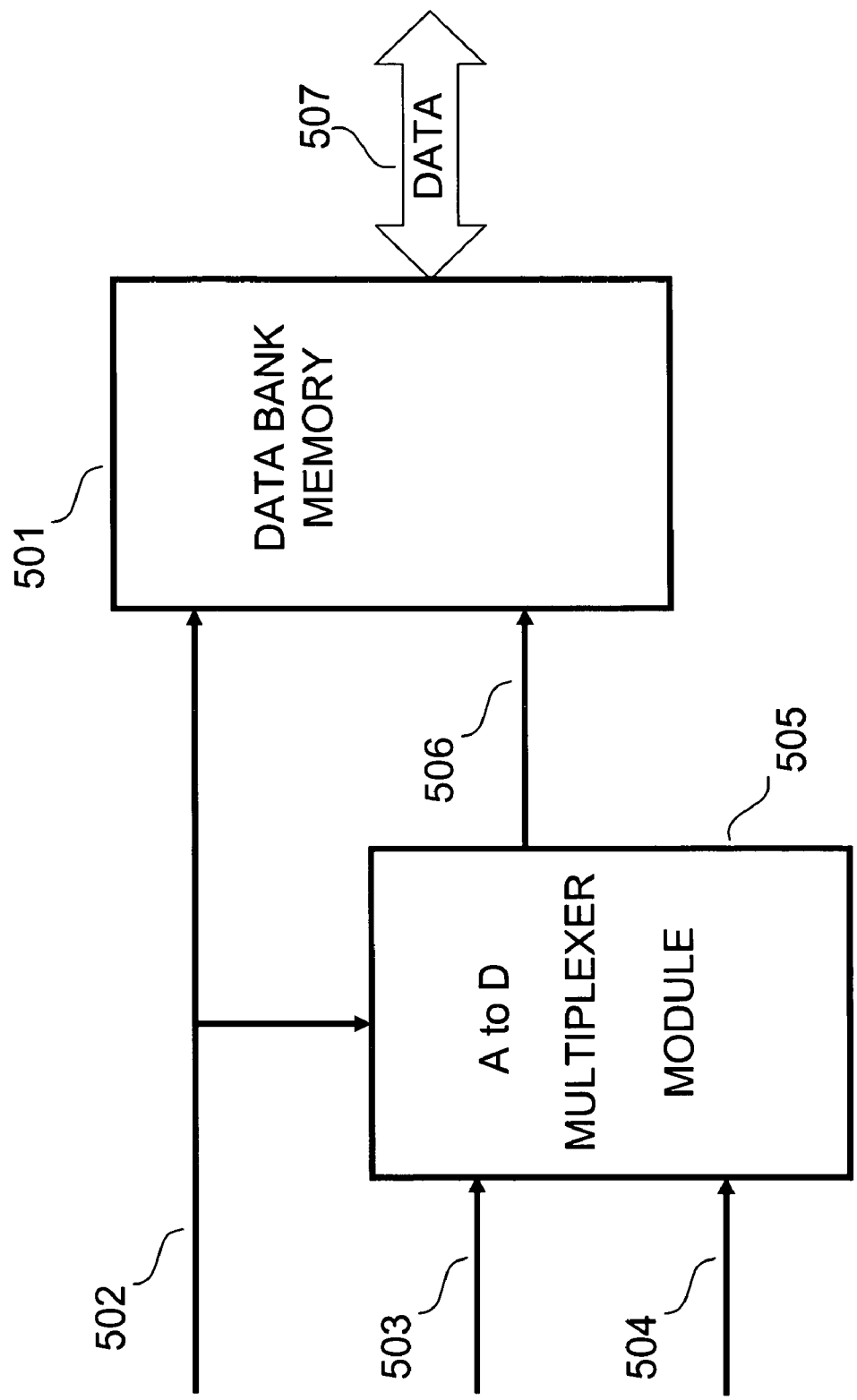
FIG. 5 illustrates a digitizing and multiplexing module and a data bank memory.

A configuration that allows the electronic processing system 105, of FIG. 1, to process the various electronic signals is illustrated in FIG. 5, where a data bank 501 stored in memory such as flash memory, with storage capacity of the order of 256 mega bytes. Mode control data 502 is used select specific environmental signals 503 or interference signals 504 by means of a module containing analog to digital converters (A to D) and multiplexers. This A to D multiplexer module 505 digitizes and makes available the selected signals as address data 506 which is combined with the mode data 502 to address the data bank memory 501.

The output data 507 of the data bank memory is made available to the electronic processing system 105 (of FIG. 1). The output data 507 can be correction data or glucose level data depending on the mode data 502 and the corresponding signal related address data 506. The mode select data can include selecting between most and least significant bytes to allow the greater accuracy than the conventional eight or sixteen bit bytes.

The data bus of the output data 507 is a bi-directional data bus, allowing information, such as, the determined glucose level, the environmental conditions and time of measuring related to the glucose level determination, and the figure of merit, to be stored in the data bank memory for future analysis and use. The current glucose level, determined by the correlation and processing techniques described above, may be displayed, used to trigger an alarm, or transmitted, for example, by wireless technology for remote monitoring or data logging.

Figure 6:
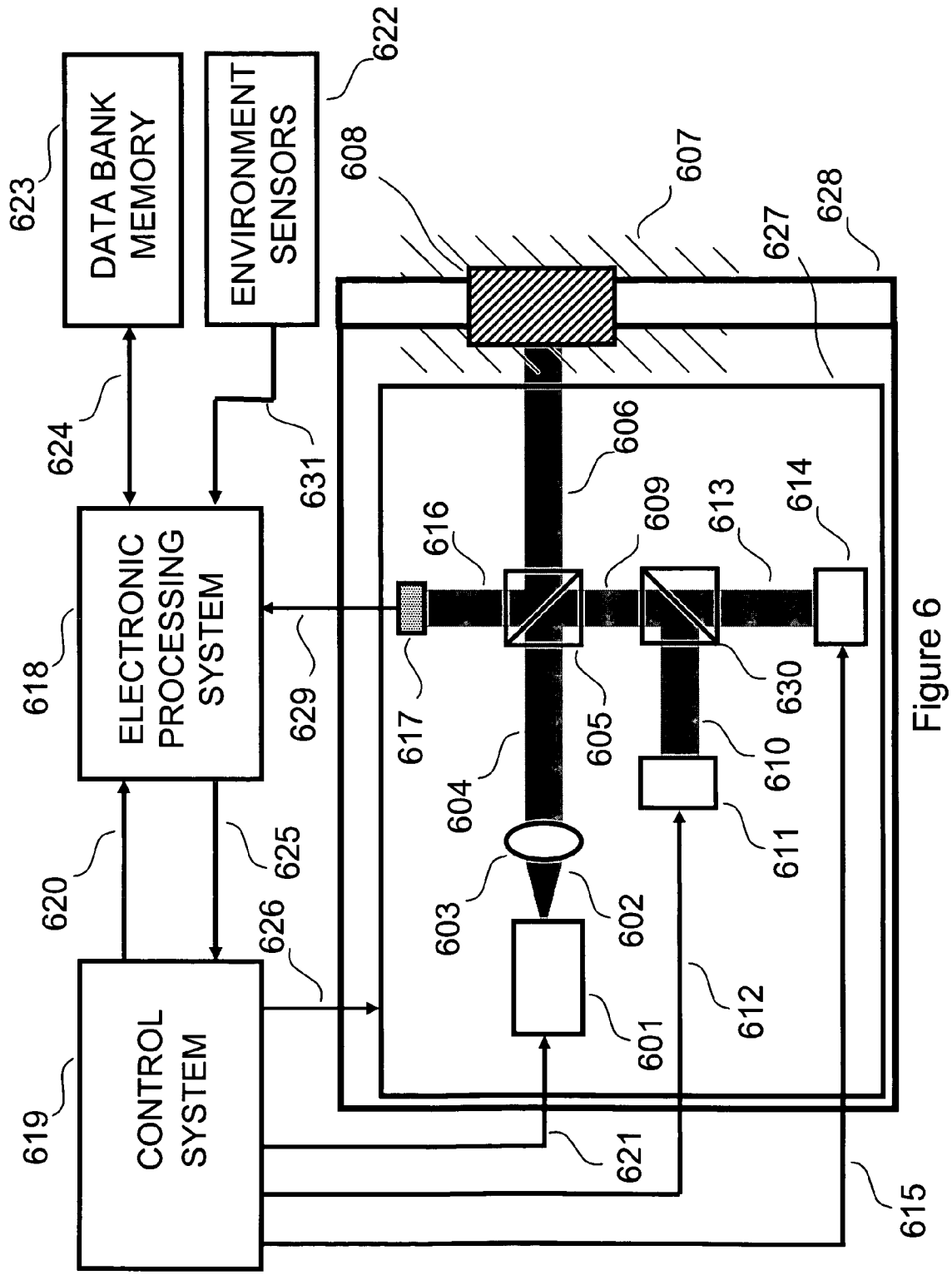
FIG. 6 illustrates an alternative embodiment of the non-invasive analysis system.

An alternative embodiment is illustrated in FIG. 6. As in the preferred embodiment, an optical source 601, such as, an SLD, LED or a mode-locked laser, generates radiation 602 which is collimated to be broad area radiation by an optical lens 603 (or an optical lens system). The collimated broad area radiation 604 is directed through a first beam-splitter 605 and a first portion of the collimated broad area radiation 606 is applied to the target 607 by means of an optional steering mirror 608 to generate back-scattered radiation within the target.

A second portion 609 of the broad area radiation 604, is directed by the first beam-splitter 605 to a second beam-splitter 630 which separates the radiation into a first and second reference radiation beam. The first reference radiation beam 610 is reflected by a modulating reflective element 611 whose modulating frequency is controlled by the control signal 612. The second reference radiation beam 613 is reflected by a modulating reflective element 614 whose modulating frequency is controlled by the control signal 615. The modulating reflective elements 611 and 614 could modulate by means of phase modulators or piezo devices (as described in an application incorporated herein by reference).

The relative optical path lengths of the first and second reference radiation 610 and 613 determine the difference in depths within the target that the associated interference signals correspond to. The modulating control signals 612 and 615 have different frequency content, allowing the associated interference signals to be separated by electronic filtering.

The modulated reflected first and second reference radiation is re-combined in the beam-splitter 630 (which also acts as a beam-combiner). The re-combined reference radiation 609 is directed back to the first beam-splitter 605 (which also acts as a beam-combiner), where it is combined with a portion of the back-scattered radiation generated in the target, to produce a composite interference signal 616 which contains interferometric information from two depths within the target.

The composite interference signal 616 is detected by the opto-electronic detector 617. The opto-electronic detector 617 is a multi-segment detector illustrated further in FIG. 3 which therefore detects spatially separated interference signals. The output signals from the multi-segment detector, i.e. the spatially separated interference signals 629, are fed to the processing system 618. The control system 619 controls the optical source 601 and the modulating reflective elements 611 and 614 by means of signals 621, 612 and 615.

The control system 619 also supplies the processing system 618 with timing signals 620 that allow the processing system to separate information associated with interference signals corresponding to different depth locations. This electronic filtering allows spatially separated information, corresponding to different depths, to be extracted from each of the interference signals detected by the multi-segment detector.

As in the preferred embodiment the processing system 618 also receives environmental signals 631 from sensors 622 such as strain gauges and temperature sensors to compensate for the influence of the environmental factors which is done in conjunction with previously stored depth correction data retrieved from the memory data bank 623 by means of a conventional address/data bus 624. The retrieved depth correction data is used to modify sample timing signals or correct the measured interference signal intensities.

The processing system 618 also intensity corrects the detected spatially separated interference signals as described before. The processing system 618 normalizes the detected spatially separated interference signals by combining the intensity correction data and the depth correction data with the measured intensities of the detected spatially separated interference signals. The normalized detected spatially separated interference signal intensities are correlated with data from a data bank stored in memory.

The correlation data is processed to determine the glucose level or concentration (the attribute) of the tissue (the target) and can also be processed to align the probe signal with respect to locating characteristics or marks on the skin surface by generating alignment information 625 which is sent to the control system 619. The control system generates alignment signals 626 which are used to move the optical processing system 627 with respect to a frame 628 by conventional means, such as electro-mechanical means.

Figure 7:
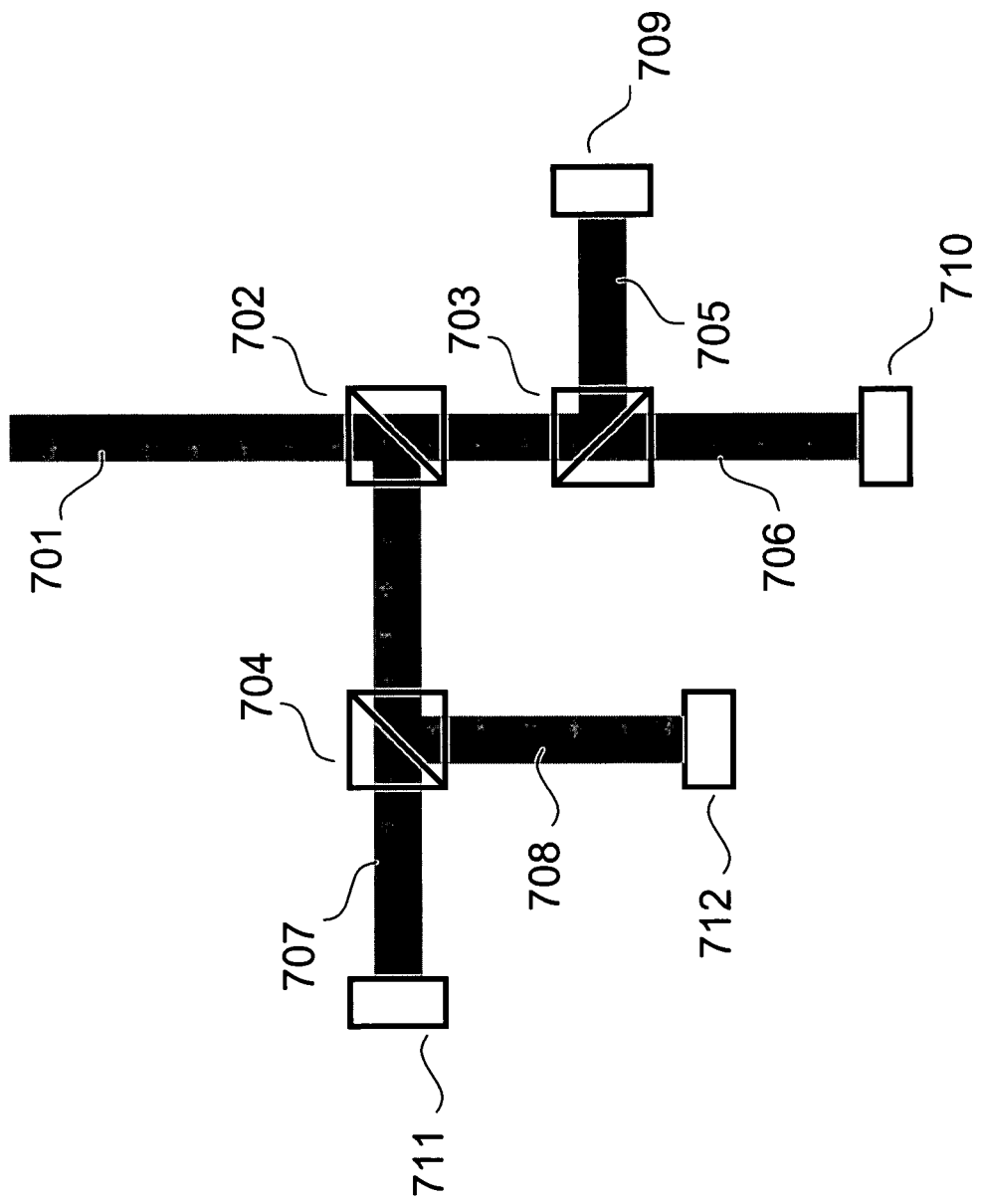
FIG. 7 illustrates a compound reflective system with four reflective elements.

In other embodiments, interference signals from additional depth levels can be acquired by using more than two modulating reflective elements. The multiple reference beam aspect in an embodiment suitable for acquiring interference signals from four different depths for each detector segment is illustrated in FIG. 7. The radiation 701 split off from the probe radiation is split into four reference beams by means of three beam-splitters 702, 703 and 704. The four reference beams 705, 706, 707 and 708 are reflected by four modulating reflective elements 709, 710, 711 and 712 each of which are modulated at a different frequency.

Figure 8A:
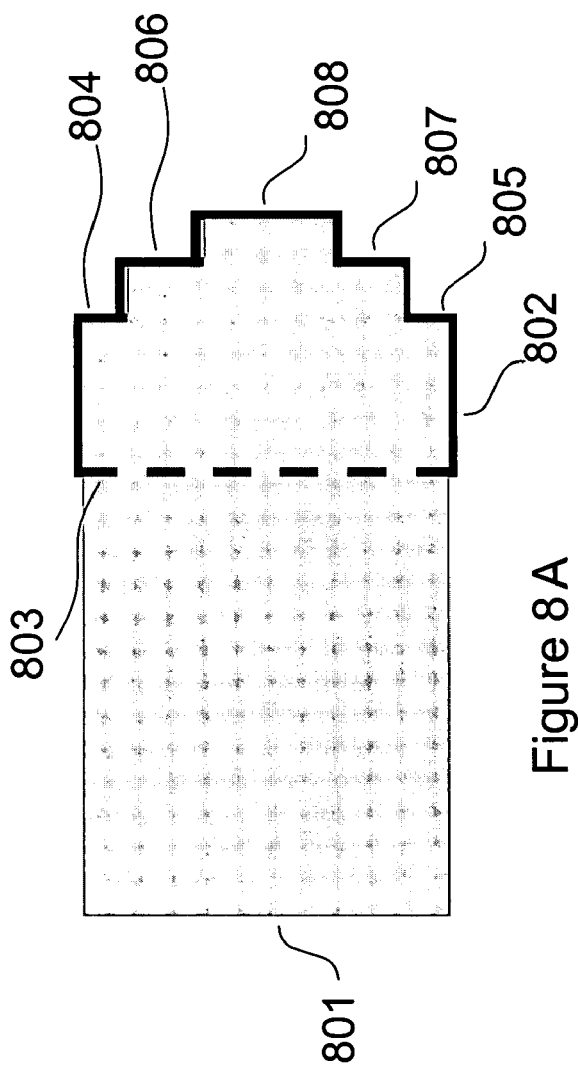
FIG. 8 illustrates a reflective element with different depth zones.

In another alternative embodiment, one or more modulating reflective elements can have zones (or segments) that define different optical path lengths and thereby generate interference signals corresponding to different depths. This aspect is illustrated in FIG. 8A where a side view of an expanded view of reference radiation 801 is directed at a compound or zonal reflective element 802 whose front surface 803, indicated by the dashed line, typically has an anti-reflective coating.

The rear surface has multiple reflecting surfaces, with reflective surfaces 804 and 805 constituting a first zone, reflective surfaces 806 and 807 constituting a second zone and surface 808 constituting a third zone. These zones are further illustrated in FIG. 8 B where a rear view of the zonal reflective element where the first zone 809, the second zone 810 and the third zone 811 are shown.

Figure 8C:
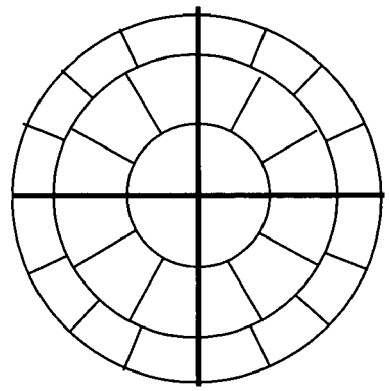
Figure 8B:
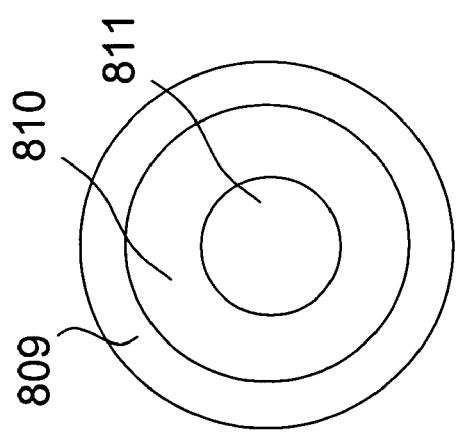

These zones are designed to match the multi-segment detector, shown again in FIG. 8C. The third zone 811 matches the central four quadrant detector segments of the multi-segment detector and the first zone 809 matches the outer ring of sixteen detector segments, while the second zone matches the remaining twelve detector segments. These multiple zone (or multiple level) reflective elements can be used in combination with single level reflective elements (with only a single zone) and may be modulated using the previously described phase modulation and piezo modulation techniques.

Another embodiment could use a single multiple zone reflector and translation of the complete optical processing system with respect the target by conventional translational techniques, such as electro-mechanical voice coils. Translation generates interference signals at a frequency determined by the translation speed. This approach has the advantage of not requiring a phase modulator or a piezo modulator.

Many combinations of the approaches to the reflective elements and modulating them are possible in order to optimize a specific application. For purposes of this application a compound reflective system includes: multiple single zone reflective elements and beam-splitters, as, for example, illustrated in FIG. 7; a single multiple zone reflective element, as, for example, illustrated in FIGS. 8A and 8B; more than one multiple zone reflective element and beam splitters; combinations of single zone and multiple zone reflective elements.

Such a compound reflective system generate reference radiation that enables generating concurrent interference signals which contains three dimensional spatially separated information. Extracting spatially separated information includes detecting the interference signals by means of a multi-segment detector and further separating information related to different depths from different interference signals by means of electronic filtering.

Figure 9:
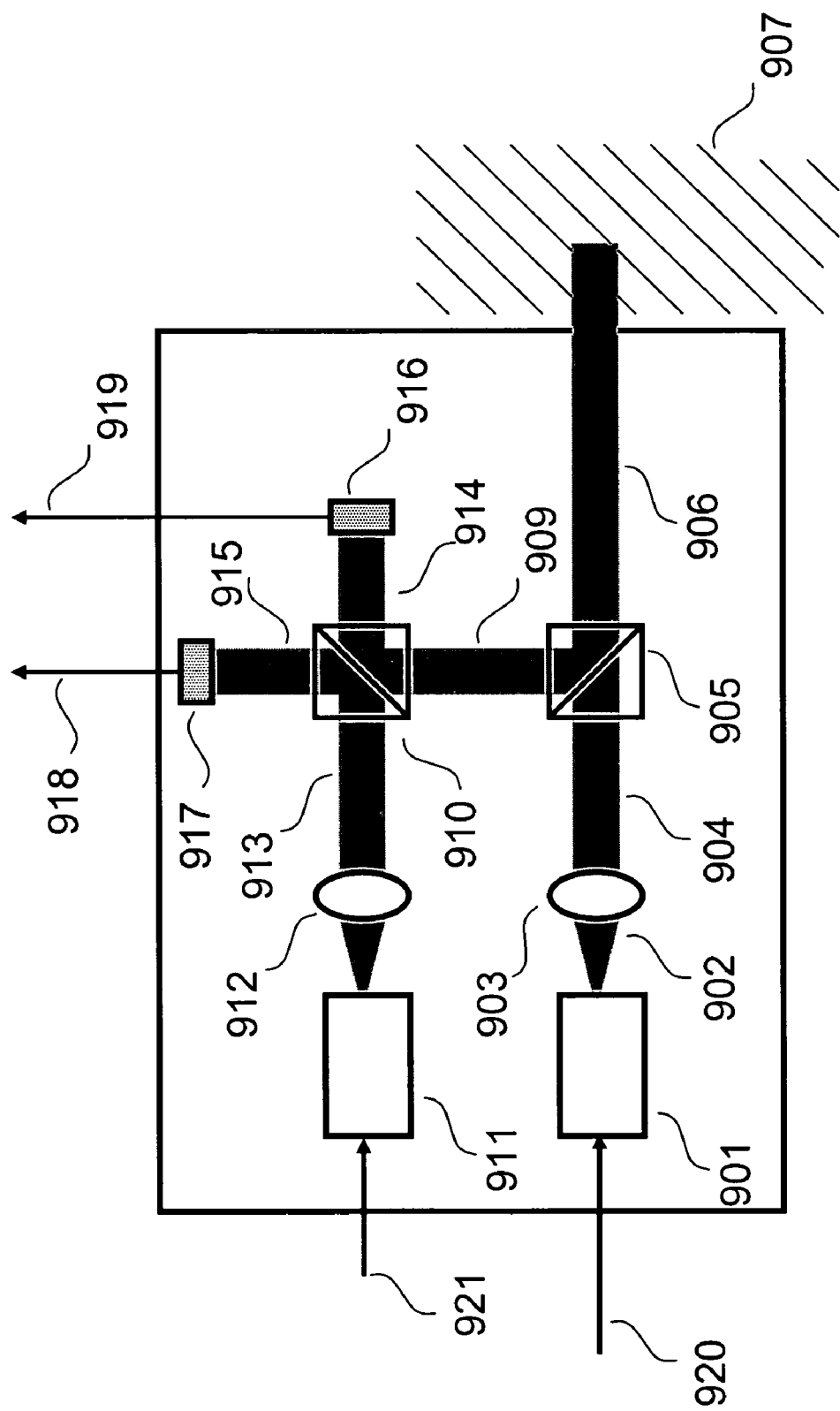
FIG. 9 illustrates an alternative embodiment of optical aspects of the system.

Yet another embodiment of the optical system is illustrated in FIG. 9. A first optical source 901, such as a first mode-locked laser, generates probe radiation 902 which is collimated to a broad area beam by an optical lens 903 (or an optical lens system). The broad area collimated probe radiation 904 is directed through a beam-splitter 905 and a portion of the broad area collimated probe radiation 906 is applied to the target 907.

Back-scattered radiation is generated in the target and a portion of the back-scattered radiation is re directed by the beam-splitter 905 to a second beam-splitter 910 and this re-directed portion of the back-scattered radiation is labeled 909. A second optical source 911, such as a second mode-locked laser, whose output is similarly collimated by an optical lens 912 (or an optical lens system) to form broad area collimated scanning reference radiation 913.

The scanning reference radiation 913 and the portion of the back-scattered radiation 909 are combined in the beam-splitter 910 (which also acts as a beam combiner) to produce complimentary interferometric signals 914 and 915 which are detected by the opto-electronic detectors 916 and 917. The opto-electronic detectors are multi-segment detectors which therefore detect spatially separated interference signals.

The output signals from the multi-segment detectors, i.e. the spatially separated interference signals 918 and 919, are fed to the processing system as in previous embodiments. In this embodiment, very high speed electronic depth scanning can be accomplished by using mode-locked lasers as optical sources 901 and 911. Optical source 901 is a probe laser and optical source 911 is a reference laser.

By mode-locking the probe and reference laser diodes at different frequencies, meaningful interference signals from sequentially varying depths within the target are generated at a repetition frequency determined by the difference in mode-locking frequencies. Mode-locking can be accomplished by applying RF signals 921 and 920 to the optical sources 901 and 911. These electronic RF signals can have a frequency difference of the order of Mega Hertz.

This enables electronic depth scanning at very high speeds with respect to motion artifacts in the target. In this embodiment, although information is acquired from different depths sequentially (rather than simultaneously), it is concurrent information because the sequential information is acquired at high speed and is therefore insensitive to motion.

The electronic depth scanning is further described in a patent application incorporated herein by reference. As in other embodiments, the detected interference signals 918 and 919 may be compensated for environmental factors, normalized and correlated with previously stored fiducial maps to generate a measurement of an attribute of the target.

The above description of the preferred embodiment illustrates a glucose level monitoring application of the invention, however, the invention has many potential applications, including but not limited to: bio-metric analysis; defect analysis of artifacts; authentication of documents, such as bank notes.

In the bio-metric analysis application, identification of individuals may be made more accurate by combining a three dimensional map of skin and sub-surface tissue with conventional finger-print analysis techniques. For purposes of this application, the term "fingerprint" includes a conventional fingerprint and the three dimensional map of skin, sub-surface tissue and any substance in proximity to the surface of the skin.

Such three dimensional high speed analysis could also verify that an artificial print (adhered to a finger) is not being used and that the underlying tissue is living tissue. In this application, the data bank memory may be a large centralized disk based storage system. Communication with the data bank could be by means of conventional wireless techniques or by conventional intra-net or internet communication techniques.

In the defect analysis application, artifacts such as, plastic or ceramic parts, biological enzymes, or semiconductor components can be analyzed to ensure they are defect free. Registration marks could be the edges and surfaces of a defect free artifact. The fiducial maps would contain interference signal data corresponding to defect free artifacts and could be stored in readily updatable central disk. The correlation figure of merit, in this application could be used to reject or accept an artifact, typically in a production line environment.

In the bank note authentication application, an advantage of this approach is that internal sub-surface or embedded characteristics can be analyzed and used to authenticate the note. In this application, registration marks can be consistent marks on the surfaces of the bank note, fiducial maps can be representations of different denomination notes, the figure of merit can be used to determine whether or not the target note is an authentic version of a particular denomination, while environment sensors could measure temperature or humidity.

In general, for purposes of this application, the term figure of merit includes any function of correlation data is that is related to the reliability or accuracy with which an attribute can be determined. Functions of correlation data suitable for determining a figure of merit include, but are not limited to, a mean deviation of the correlation data, and a mean deviation of a subset of the correlation data. In both the calibration process and determining the attribute of the target the correlation data is processed to generate a figure of merit.

The figure of merit can then be used to used to indicate the status of a monitor. The status of the monitor includes, but is not limited to, monitor re-calibration required, or increased reliance on the monitor permitted. The status may be indicated by means of a display, or other communication method or by enabling or disabling one or more function or capabilities of the monitor.

It is understood that the above description is intended to be illustrative and not restrictive. Many of the features have functional equivalents that are intended to be included in the invention as being taught. Many variations and combinations of the above embodiments are possible, for example, other environmental sensors, such as pulse rate or humidity could be used, various combinations and mechanical configurations can be used.

Broad area radiation could be generated by an array of optical sources, such as a VCSEL array (Vertical Cavity Surface Emitting Laser array), an SLD array or an LED array rather than a single optical source. Such arrays could be collimated by an array of micro-lens, which could be spatially matched with a multi-segment detector. An advantage of using such arrays is that there is reduced sensitivity to cross-talk between adjacent optical signals because they are incoherent with respect to each other. The first and second mode-locked lasers could be mode-locked laser diodes or mode-locked micro-lasers.

The multi-segment detectors illustrated are two dimensional and have a high degree of symmetry. Many other topologies can be used including less symmetric ones and one dimensional segment arrays. The one dimensional segment array would provide two dimensional concurrent information. Sets of two dimensional concurrent information could be acquired by translating the optical system by conventional means to provide three dimensional sets of information. Similarly, a single segment detector could be used to provide one dimensional concurrent information and sets of one dimensional concurrent information could be acquired by translating the optical system by conventional means to provide two or three dimensional sets of information.

Beam splitters could be output couplers with either wedged or parallel surfaces. Pellicles could also be used as beam splitters. The illustrated versions of this invention are free space implementations. Equivalent fiber based versions of this invention are also intended to be included. In fiber based embodiments fiber splitters may be used as beam splitters and fiber Bragg gratings or fiber loops used as reflective elements.

In addition to the examples for generating a multiple reference beam, also referred to herein as a composite reference beam, illustrated in FIGS. 2, 6 and 7 there are many other variations and implementations possible. For example, referring to FIG. 2, the position of the partial reflective element 211 could be modulated and the reflective element 214 could be not modulated, or both elements 211 and 214 could both be modulated. Element 214 could also be a partial reflective element. In general, the composite reference radiation is generated by means of at least two reflective elements and at least one modulating element.

Other applications can be addressed. For example, an imaging application could involve repeatedly generating and storing interference signal data sets under different environmental conditions. The stored data sets become the fiducial maps for future analysis and facilitate monitoring for abnormal changes in, for example, tissue. Analyzing for such changes provides a method of routine monitoring for or the progress of malignant conditions, such as skin cancer or the progress of healing after traumatic damage, such as, burns.

The embodiments described use optical radiation, however the invention is not restricted to optical radiation. The invention could use other forms of radiation, including but not limited to, acoustic radiation such as ultra-sound, and other forms of electromagnetic radiation such as micro-wave or x-ray radiation.

With or without the use of fiducial maps, the imaging application, can avail of the concurrent detection of multiple spatially separated interference signals captured by the multi-segment detector. Use of multiple reflective elements enables depth scanning at increased speeds. This enables a high speed imaging technique that is insensitive to motion artifacts.

The scope of this invention should therefore not be determined with reference to the above description, but instead should be determined with reference to the appended claims and drawings, along with the full scope of equivalents to which such claims and drawings are entitled.

What is claimed is:

1. A method of determining an attribute of a target, comprising:
   generating probe radiation;
   applying at least a portion of said probe radiation to said target to generate back-scattered radiation;
   generating reference radiation;
   combining said back-scattered radiation and said reference radiation to produce an interference signal;
   detecting said interference signal by means of a detector;
   extracting concurrent information from said detected interference signal;
   correlating said extracted concurrent information with data from a data bank stored in memory to generate correlation data; and
   processing said correlation data to determine said attribute of said target.

2. The method of claim 1, wherein the extracted concurrent information is normalized.

3. The method of claim 1, wherein the extracted concurrent information is modified using data related to environment sensor signals.

4. The method of claim 1, wherein the target is tissue.

5. The method of claim 1, wherein the attribute is a glucose concentration level.

6. The method of claim 1, wherein the attribute is a bio-metric characteristic.

7. The method of claim 1, wherein the attribute is an image of the target.

8. The method of claim 1, wherein the correlation data is processed to generate a figure of merit.

9. The method of claim 8, wherein the figure of merit is used to indicate the status of a monitor.

10. The method of claim 1, wherein a portion of the probe radiation which is applied to the target is aligned with registration marks associated with the target.

11. The method of claim 1, wherein extracting concurrent information from the detected interference signal is accomplished by means of electronic filtering.

12. The method of claim 1, wherein extracting concurrent information from the detected interference signals is accomplished by sampling the interference signals at specific times.

13. The method of claim 1, wherein the detector is multi-segment detector.

14. The method of claim 1, wherein extracting concurrent information from the detected interference signal is accomplished by means of the segmented nature of the detector.

15. The method of claim 1, wherein the probe radiation is generated by a superluminescent diode.

16. The method of claim 1, wherein the probe radiation is generated by a mode-locked laser.

17. The method of claim 1, wherein the probe radiation is acoustic radiation.

18. The method of claim 1, wherein the probe radiation is generated by an array of optical sources.

19. The method of claim 1, wherein the reference radiation is a portion of the generated probe radiation.

20. The method of claim 1, wherein the reference radiation is composite reference radiation.

21. The method of claim 20, wherein the composite reference radiation is generated by means of at least two reflective elements and at least one modulating element.

22. An apparatus for determining an attribute of a target, comprising:
   means for generating probe radiation;
   means for applying at least a portion of said probe radiation to said target to generate back-scattered radiation;
   means for generating reference radiation;
   means for combining said back-scattered radiation and said reference radiation to produce an interference signal;
   means for detecting said interference signal by means of a detector;
   means for extracting concurrent information from said detected interference signal;
   means for correlating said extracted concurrent information with data from a data bank stored in memory to generate correlation data; and
   means for processing said correlation data to determine said attribute of said target.

23. The apparatus of claim 22, wherein the extracted concurrent information is normalized.

24. The apparatus of claim 22, wherein the extracted concurrent information is modified using data related to environment sensor signals.

25. The apparatus of claim 22, wherein the target is tissue.

26. The apparatus of claim 22, wherein the attribute is a glucose concentration level.

27. The apparatus of claim 22, wherein the attribute is a bio-metric characteristic.

28. The apparatus of claim 22, wherein the attribute is an image of the target.

29. The apparatus of claim 22, wherein the correlation data is processed to generate a figure of merit.

30. The apparatus of claim 29, wherein the figure of merit is used to indicate the status of a monitor.

31. The apparatus of claim 22, wherein a portion of the probe radiation which is applied to the target is aligned with registration marks associated with the target.

32. The apparatus of claim 22, wherein extracting concurrent information from the detected interference signal is accomplished by means of electronic filtering.

33. The apparatus of claim 22, wherein extracting concurrent information from the detected interference signals is accomplished by sampling the interference signals at specific times.

34. The apparatus of claim 22, wherein the detector is multi-segment detector.

35. The apparatus of claim 22, wherein extracting concurrent information from the detected interference signal is accomplished by means of the segmented nature of the detector.

36. The apparatus of claim 22, wherein the probe radiation is generated by a superluminescent diode.

37. The apparatus of claim 22, wherein the probe radiation is generated by a mode-locked laser.

38. The apparatus of claim 22, wherein the probe radiation is acoustic radiation.

39. The apparatus of claim 22, wherein the probe radiation is generated by an array of optical sources.

40. The apparatus of claim 22, wherein the reference radiation is a portion of the generated probe radiation.

41. The apparatus of claim 22, wherein the reference radiation is composite reference radiation.

42. The apparatus of claim 41, wherein the composite reference radiation is generated by means of at least two reflective elements and at least one modulating element.

43. A system for determining an attribute of a target, the system comprising:

an optical system operable to generate probe radiation and reference radiation, said optical system configured to apply at least a portion of said probe radiation to said target to generate back-scattered radiation and configured to combine said back-scattered radiation with said reference radiation to produce an interference signal;

a detector operable to detect said interference signal;

a control system operable to control said optical system and an electronic processing system;

a memory storing data in a data bank;

said electronic processing system operable to extract concurrent information from said detected interference signal, to correlate said extracted concurrent information with said data to generate correlation data, and wherein said correlation data is further processed by said electronic processing system to determine said attribute of said target.

44. A system as in claim 43 further comprising environment sensors.

* * * * *